(12) United States Patent
Dietz et al.

(10) Patent No.: US 8,236,788 B2
(45) Date of Patent: Aug. 7, 2012

(54) AZOLYLMETHYLOXIRANES, USE THEREOF FOR CONTROLLING PLANT PATHOGENIC FUNGI, AND AGENTS CONTAINING THE SAME

(75) Inventors: Jochen Dietz, Mannheim (DE); Thomas Grote, Wachenheim (DE); Bernd Müller, Frankenthal (DE); Jan Klaas Lohmann, Ludwigshagen (DE); Jens Renner, Bad Dürkheim (DE); Sarah Ulmschneider, Bad Dürkheim (DE); Alice Glättli, Mannheim (DE)

(73) Assignee: BASF SE, Ludwigshafen (DE)

( * ) Notice: Subject to any disclaimer, the term of this patent is extended or adjusted under 35 U.S.C. 154(b) by 99 days.

(21) Appl. No.: 12/374,710

(22) PCT Filed: Jul. 18, 2007

(86) PCT No.: PCT/EP2007/057404
§ 371 (c)(1),
(2), (4) Date: Jan. 22, 2009

(87) PCT Pub. No.: WO2008/012246
PCT Pub. Date: Jan. 31, 2008

(65) Prior Publication Data
US 2009/0270256 A1    Oct. 29, 2009

(30) Foreign Application Priority Data
Jul. 24, 2006  (EP) ..................................... 06117716

(51) Int. Cl.
*A61K 31/41* (2006.01)
*A01N 43/653* (2006.01)
*C07D 249/08* (2006.01)

(52) U.S. Cl. ..... 514/184; 514/383; 548/101; 548/262.2; 548/266.6

(58) Field of Classification Search .................. 514/184, 514/383; 548/101, 262.2, 266.6
See application file for complete search history.

(56) References Cited

U.S. PATENT DOCUMENTS

| | | | |
|---|---|---|---|
| 4,061,656 A | 12/1977 | Klaus et al. | |
| 4,116,975 A | 9/1978 | Klaus et al. | |
| 4,464,381 A * | 8/1984 | Janssen et al. | 514/382 |
| 4,652,580 A * | 3/1987 | Janssen et al. | 514/383 |
| 4,723,042 A | 2/1988 | Janssen et al. | |
| 4,804,785 A | 2/1989 | Janssen et al. | |
| 4,906,652 A * | 3/1990 | Karbach et al. | 514/383 |
| 4,914,128 A | 4/1990 | Schirmer et al. | |
| 4,935,245 A * | 6/1990 | Horn et al. | 424/489 |
| 5,118,511 A * | 6/1992 | Horn et al. | 424/502 |
| 5,162,357 A * | 11/1992 | Seele et al. | 514/383 |
| 6,211,387 B1 | 4/2001 | Napoletano et al. | |
| 6,277,791 B1 | 8/2001 | Assmann et al. | |
| 6,313,147 B1 | 11/2001 | Shaber et al. | |
| 6,372,692 B1 | 4/2002 | Assmann et al. | |
| 6,448,228 B1 | 9/2002 | Filippini et al. | |
| 6,642,181 B2 | 11/2003 | Assmann et al. | |
| 6,812,229 B1 | 11/2004 | Ozaki et al. | |
| 6,875,783 B2 | 4/2005 | Assmann et al. | |
| 7,098,227 B2 | 8/2006 | Dunkel et al. | |
| 7,157,481 B2 | 1/2007 | Assmann et al. | |
| 2006/0178374 A1 | 8/2006 | Cui et al. | |
| 2007/0232670 A1 | 10/2007 | Assmann et al. | |
| 2009/0197929 A1 | 8/2009 | Dietz et al. | |
| 2009/0203700 A1 | 8/2009 | Dietz et al. | |
| 2009/0305887 A1 * | 12/2009 | Dietz et al. | 504/100 |
| 2010/0087321 A1 * | 4/2010 | Renner et al. | 504/272 |
| 2010/0167924 A1 * | 7/2010 | Dietz et al. | 504/100 |
| 2010/0179058 A1 * | 7/2010 | Dietz et al. | 504/100 |

FOREIGN PATENT DOCUMENTS

| | | |
|---|---|---|
| CA | 2 011 087 | 9/1990 |
| CA | 2 012 596 | 9/1990 |
| CA | 2 048 974 | 3/1992 |
| CA | 2 287 470 | 10/1998 |
| DE | 2651968 | 5/1977 |
| DE | 3601927 | 7/1987 |
| DE | 3942333 | 6/1991 |
| EP | 0 094 564 | 11/1983 |
| EP | 0135122 | 3/1985 |
| EP | 0 174 769 | 3/1986 |

(Continued)

OTHER PUBLICATIONS

International Preliminary Report on Patentability for International Application No. PCT/2007/057404; International Filing Date: Jul. 18, 2007; Date of Issuance: Jan. 27, 2009.

(Continued)

*Primary Examiner* — Susannah Chung
(74) *Attorney, Agent, or Firm* — Brinks Hofer Gilson & Lione

(57) ABSTRACT

The present invention relates to azolylmethyloxiranes of the general formula I (I)

in which
A or B is phenyl which is substituted by one CN and optionally by one to three of the following substituents: halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and the respective other substituent
A or B is phenyl or 5-membered or 6-membered heteroaryl, these substituents optionally being substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and to the plant-compatible acid addition salts or metal salts thereof, to the use of the compounds of the formula I for controlling phytopathogenic fungi and to compositions comprising these compounds.

10 Claims, No Drawings

FOREIGN PATENT DOCUMENTS

| | | |
|---|---|---|
| EP | 0 196 038 | 10/1986 |
| EP | 226 917 | 7/1987 |
| EP | 0 386 557 | 9/1990 |
| EP | 0 388 871 | 9/1990 |
| EP | 0 421 125 | 4/1991 |
| EP | 0 474 045 | 3/1992 |
| EP | 1028125 | 8/2000 |
| EP | 1201648 | 5/2002 |
| WO | WO 92/05145 | 4/1992 |
| WO | WO 98/46608 | 10/1998 |
| WO | WO 99/24413 | 5/1999 |
| WO | WO 99/29645 | 6/1999 |
| WO | WO 03/014103 | 2/2003 |
| WO | WO 03/053145 | 7/2003 |
| WO | WO 03/066609 | 8/2003 |
| WO | WO 2004/049804 | 6/2004 |
| WO | WO 2006021886 | 3/2006 |

OTHER PUBLICATIONS

Bazzini, Cristina, et al., "Synthesis and Characterization of Some Aza[5]helicenes", Eur. J. Org. Chem, 2005, 1247-1257.

Evans, Owen R., et al., "Rational Design of Nonlinear Optical Materials Based on 2D Coordination Networks", Chem. Matter, 2001, p. 3009-3017, vol. 13.

Hameka, Hendrik, F., "Computation of the Structures of the Phenyl and Benzyl Radicals with the UHF Method", J. Org. Chem., 1987, p. 5025-5026, vol. 52.

Marquis, Annie et al., "Messages in Molecules: Ligand/Cation Coding and Self-Recognition in a Constitutionally Dynamic System of Heterometallic Double Helicates", Chemistry Euro J, 2006, p. 5632-5641, vol. 12.

Shizuka, Haruo et al., "Excited-State Proton-Transfer Reactions of Naphthylammonium Ion-18-Crown-6 Complexes", J. Am. Chem. Soc., 1985, p. 3956-3963, vol. 107.

Tsuge, Akihiko, et al., "Self-assembled coordination cage derived from small-sized pyridinophane", Tetrahedron Letters, 2006, p. 6607-6609, vol. 47.

Office Action dated May 5, 2010, from U.S. Appl. No. 12/306,322.
Office Action dated Jul. 29, 2010, from U.S. Appl. No. 12/306,027.
Office Action dated May 5, 2010, from U.S. Appl. No. 12/306,339.

International Preliminary Report on Patentability for International Application No. PCT/EP2007/057404; International Filing Date: Jul. 18, 2007; Date of Issuance: Feb. 17, 2009.

Banwell et al., "Utilization of 1-aryl-2,2-dibromocyclopropanes in synthetic approaches to phenanthroquinolizidine and phenanthroindolizidine alkaloids", Australian Journal of Chemistry, 57(6), 537-548 (2004).

Clinch et al., "Synthesis of substituted tetrahydropyridines and m-hydroxybenzoic acids", Tetrahedron, 45(1), 239-258 (1989).

Xavier Creary, "Reaction of organometallic reagents with ethyl trifluoroacetate and diethyl oxalate. Formation of trifluoromethyl ketones and α-keto esters via stable tetrahedral adducts", Journal of Organic Chemistry, 52(22), 5026-2030 (1987).

Hadfield et al., "Synthesis and evaluation of double bond substituted combretastatins", European Journal of Medicinal Chemistry, 40(6), 529-541 (2005).

Hammer et al., "Stereoselective Synthesis of thiophenedimethyl-and benzenedimethyl- α,α'-bridged bis(glycines)", Acta Chemical Scandinavica, 51(3), 392-402 (1997).

Heuser et al., "Synthesis of novel cyclopropylic sulfones and sulfonamides acting as glucokinase activators", Tetrahedron Letters, 47(16), 2675-2678 (2006).

Klett et al., "Cumulene photochemistry: Photorearrangements of tetraphenyl and triphenyl $C_3$ isomers", Journal of the American Chemical Society, 107(13), 3963-3971 (1985).

Mali et al., "Useful Synthesis of Coumestans", Synthetic Communications, 20(12), 1781-1791 (1990).

Ogle et al., "Chiral lithiothiophenes as non-transferable ligands in organocuprate conjugate addition reactions", Tetrahedron: Asymmetry, 14(21), 3281-3283 (2003).

Romo et al., "Diastereoselective cyclopropanations of chiral bicyclic lactams leading to enantiomerically pure cyclopropanes. Application to the total synthesis of CIS-(1S, 3R)-deltamethrinic acid and R-(−)-dictyopterene C'", Tetrahedron, 46(13-14), 4951-4994 (1990).

Shimizu et al., "Effective synthesis of tamoxifen using nickel-catalyzed arylative carboxylation", Synlett, (18), 3182-3184 (2006).

Tessier et al., "(Z)-Tamoxifen and tetrasubstituted alkenes and dienes via a region- and stereopsecific three-component magnesium carbometalation palladium (0) cross-coupling strategy", Organic Letters, 5(17), 2989-2992 (2003).

Vu et al., "Stereoselective preparation of functionalized unsaturated lactones and esters via functionalized magnesium carbenoids", Synthesis, (12), 1797-1802 (2003).

Zheng et al., "Design, synthesis, and biological evaluation of the N-diarylalkenyl-poperidinecarboxylic acid derivatives as GABA uptake inhibitors (I)", Bioorganic & Medicinal Chemistry Letters, 16(1), 222-227 (2006).

International Search Report for International Application No. PCT/EP2007/057404; International Filing Date: Jul. 18, 2007; Date of Completion: Nov. 29, 2007; Date of Mailing: Jul. 12, 2007.

Epple, R. et al., "3,4,5-Trisubstituted isoxazoles as novel PPARδ agonists. Part 2", Bioorganic & Medicinal Chemistry Letters, 16, 5488-5492 (2006).

Grushin, V. et al., "Transformations of chloroarenes, catalyzed by transition-metal complexes", Chem. Rev. 94, 1047-1062 (1994).

Romines, K. et al., "Structure-activity relationship studies of novel benzophenones leading to the discovery of a potent, next generation HIV nonnucleoside reverse transcriptase inhibitor", J. Med. Chem, 49, 727-739 (2006).

Sundermeier, M. et al., "Progress in the palladium-catalyzed cyanation of aryl chlorides", Chem. Eur. J. 9:8, 1828-1836 (2003).

Zhang, X. et al., "Synthesis and SAR of novel hydantoin derivatives as selective androgen receptor modulators", Bioorganic & Medicinal Chemistry Letters, 16, 5763-5766 (2006).

* cited by examiner

AZOLYLMETHYLOXIRANES, USE THEREOF FOR CONTROLLING PLANT PATHOGENIC FUNGI, AND AGENTS CONTAINING THE SAME

This application is a National Stage application of International Application No. PCT/EP2007/057404 filed Jul. 18, 2007, the entire contents of which is hereby incorporated herein by reference. This application also claims the benefit under 35 U.S.C. §119 of European Patent Application No. 06117716.8, filed Jul. 24, 2006, the entire contents of which is hereby incorporated herein by reference.

The present invention relates to azolylmethyloxiranes of the general formula I

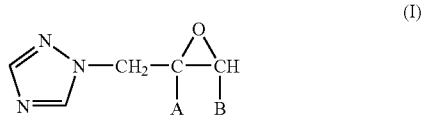

in which
A or B is phenyl which is substituted by one CN and optionally by one to three of the following substituents: halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and the respective other substituent
A or B is phenyl or 5-membered or 6-membered heteroaryl, these substituents optionally being substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio,
and to the plant-compatible acid addition salts or metal salts thereof.

Furthermore, the invention relates to the use of the compounds of the formula I for controlling phytopathogenic fungi and to compositions comprising these compounds.

Azolylmethyloxiranes, their preparation and their use in crop protection are known, for example, from EP-A 0 094 564 and EP-A 0 196 038.

Azolylmethyloxiranes which carry a hetaryl substituent on the oxirane ring are known from EP-A 0 421 125.

The azolylmethyloxiranes described already have good to very good fungicidal activity against a number of pathogens; however, it was the object of the present invention to provide novel azolylmethyloxiranes having improved fungicidal activity.

This object was achieved with the compounds of the formula I described at the outset.

Owing to the basic character of their nitrogen atoms, the compound I is capable of forming salts or adducts with inorganic or organic acids or with metal ions.

Examples of inorganic acids are hydrohalic acids, such as hydrogen fluoride, hydrogen chloride, hydrogen bromide und hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc.

Suitable metal ions are in particular the ions of the elements of the second main group, in particular calcium and magnesium, of the third and fourth main group, in particular aluminum, tin and lead and also of the elements of transition groups one to eight, in particular chromium, manganese, iron, cobalt, nickel, copper, zinc and others. Particular preference is given to the metal ions of the elements of transition groups of the fourth period. The metals can be present in the various valencies that they can assume.

The preparation of the compounds of the formula I is known and described in detail in EP-A 0 094 564, EP-A 0 196 038 and EP-A 0 421 125.

Here, the corresponding CN-substituted phenyl is prepared from an aryl halide.

The conversion of an aryl halide into the corresponding cyanide is a known reaction (see Chem. Rev. 1994, 94, 1047). Suitable aryl halides are the fluorine, chlorine, bromine and iodine compounds. The reaction can be carried out thermally using cyanides such as, for example, Cu(I)CN in high-boiling solvents such as NMP or DMF or DMSO or nitrobenzene. An example for this reaction is, for example, Bioorganic & Medicinal Chemistry Letters, 16(22), 5763-5766; 2006 or Journal of Medicinal Chemistry, 49(2), 727-739; 2006.

Alternatively, the reaction can also be carried out with metal catalysis. Suitable catalysts are various transition metal complexes, such as, for example, nickel or palladium. The cyanide source may, inter alia, be an alkali metal cyanide, such as, for example, sodium cyanide or potassium cyanide, or a transition metal cyanide, such as, for example, nickel cyanide or zinc cyanide.

Examples of palladium-catalyzed cyanations can be found in Bioorganic & Medicinal Chemistry Letters, 16(21), 5488-5492; 2006, Chem. Eur. J. 2003, 9, 1828 or WO 2006021886.

A palladium-free reaction under microwave conditions starting with aryl chlorides and aryl bromides using nickel cyanide is described in J. Org. Chem. 2003, 68, 9122-9125. Suitable solvents are DMF or NMP.

In the definitions of the symbols given in the formulae above, collective terms are used which are generally representative of the substituents below:

Halogen: fluorine, chlorine, bromine and iodine.

Alkyl and the alkyl moieties of composite groups such as, for example, alkylamino: saturated straight-chain or branched hydrocarbon radicals having preferably 1 to 4 carbon atoms, such as methyl, ethyl, propyl, 1-methylethyl, butyl, 1-methylpropyl, 2-methylpropyl and 1,1-dimethylethyl.

Haloalkyl: alkyl as mentioned above, where some or all of the hydrogen atoms in these groups are replaced by halogen atoms as mentioned above. In one embodiment, the alkyl groups are substituted at least once or completely by a particular halogen atom, preferably fluorine, chlorine or bromine. In a further embodiment, the alkyl groups are partially or fully halogenated by different halogen atoms; in the case of mixed halogen substitutions, the combination of chlorine and fluorine is preferred. Particular preference is given to ($C_1$-$C_4$)-haloalkyl, more preferably ($C_1$-$C_2$)-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

Alkoxy: an alkyl group as defined above which is attached via an oxygen, preferably having 1 to 4 carbon atoms. Examples of preferred alkoxy groups are: methoxy, ethoxy, n-propoxy, 1-methylethoxy, butoxy, 1-methylpropoxy, 2-methylpropoxy or 1,1-dimethylethoxy.

Haloalkoxy: alkoxy as defined above, where some or all of the hydrogen atoms in these groups are replaced by halogen atoms as described above under haloalkyl, in particular fluorine, chlorine or bromine. Examples of preferred haloalkoxy radicals are $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

Alkylthio: alkyl as defined above which is attached via a sulfur atom.

5-membered heteroaryl which contains one, two, three or four nitrogen atoms or one, two or three nitrogen atoms and/or one sulfur or oxygen atom, where the heteroaryl may be attached via carbon or nitrogen, if present: 5-membered heteroaryl groups which, in addition to carbon atoms, may contain one to four nitrogen atoms or one to three nitrogen atoms and/or one sulfur or oxygen atom as ring members, for example furyl, thienyl, pyrrolyl, pyrazolyl, imidazolyl, triazolyl (1,2,3-; 1,2,4-triazolyl), tetrazolyl, oxazolyl, isoxazolyl, 1,3,4-oxadiazolyl, thiazolyl, isothiazolyl and thiadiazolyl, in particular 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl.

6-membered heteroaryl which contains one, two, three or four, preferably one, two or three, nitrogen atoms, where the heteroaryl may be attached via carbon or nitrogen, if present: 6-membered heteroaryl groups which, in addition to carbon atoms, may contain one to four or one to three nitrogen atoms as members, for example pyridinyl, pyrimidinyl, pyrazinyl, pyridazinyl, 1,2,3-triazinyl, 1,2,4-triazinyl, 1,3,5-triazinyl, in particular 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The novel compounds of the formula I contain chiral centers and are generally obtained in the form of racemates or as diastereomer mixtures of erythro and threo forms. The erythro and threo diastereomers of the compounds according to the invention can be separated and isolated in pure form, for example, on the basis of their different solubilities or by column chromatography. Using known methods, such uniform pairs of diastereomers can be used to obtain uniform enantiomers. Suitable for use as antimicrobial agents are both the uniform diastereomers or enantiomers and mixtures thereof obtained in the synthesis. This applies correspondingly to the fungicidal compositions.

The compounds according to the invention may be present in various crystal modifications which may differ in their biological activity. They are likewise provided by the present invention.

In the compounds of the formula I according to the invention or in the compounds of the formula I used according to the invention, the following meanings of the substituents, in each case on their own or in combination, are particularly preferred. Here, the preferred substituents or preferred combinations of substituents apply, if appropriate, correspondingly to the precursors of the compounds according to the invention.

The substituent A or B is phenyl which is substituted by one CN and optionally additionally by one to three of the following substituents: halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

According to one embodiment, the CN substituent is located in the 4-position of the phenyl ring.

According to a further embodiment, the phenyl ring is substituted in the 2,4-position.

According to a further embodiment, A or B is phenyl which is substituted by one CN and one to three further substituents selected from one to three of the following substituents: halogen, $C_1$-$C_4$-alkyl, $C_1$-$C_4$-alkoxy, $C_1$-$C_4$-haloalkyl or $C_1$-$C_4$-haloalkoxy.

According to another embodiment, the substituent A or B is phenyl which is substituted by one CN and one to three further substituents selected from the group consisting of halogen, $C_1$-$C_4$-alkyl and $C_1$-$C_4$-alkoxy.

According to another embodiment, the substituent A or B is phenyl which is substituted by one CN and one to three halogens.

According to another embodiment, the substituent A or B is phenyl which is substituted by one CN and one of the substituents mentioned above.

In a preferred embodiment, the substituent A or B is phenyl which is substituted by one CN and a further substituent selected from the group consisting of halogen.

In a further preferred embodiment, the substituent A or B is phenyl which is substituted only by one CN.

In another preferred embodiment, the substituent A or B is phenyl which is substituted only by one CN, namely in the case of the substituent A in the 4-position and in the case of the substituent B in the 2-position.

The following substituents A, in which X is F or Cl, are particularly preferred:

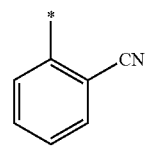

A1, B1

-continued
A2, B2
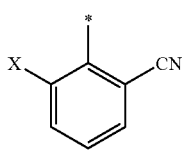
A3, B3
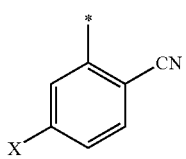
A4, B4
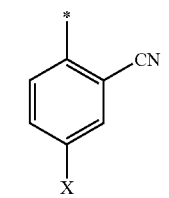
A5, B5
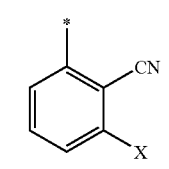
A6, B6
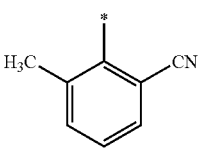
A7, B7
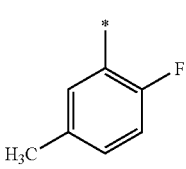
A8, B8
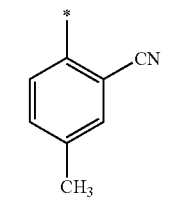
A9, B9
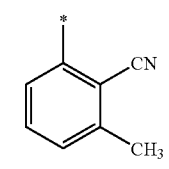
A10, B10
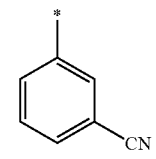
-continued
A11, B11
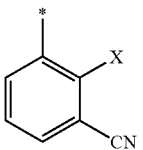
A12, B12
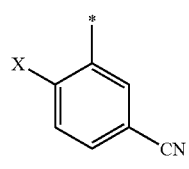
A13, B13
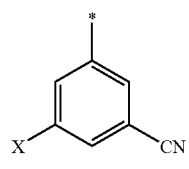
A14, B14
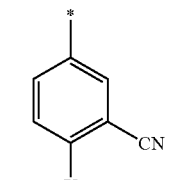
A15, B15
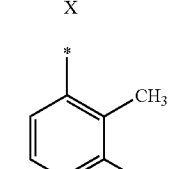
A16, B16
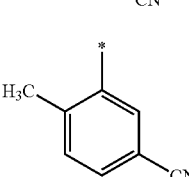
A17, B17
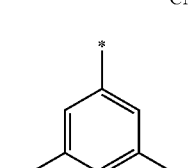
A18, B18
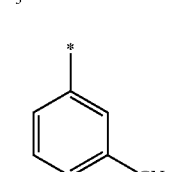
A19, B19
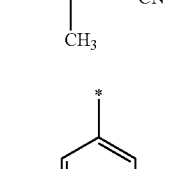

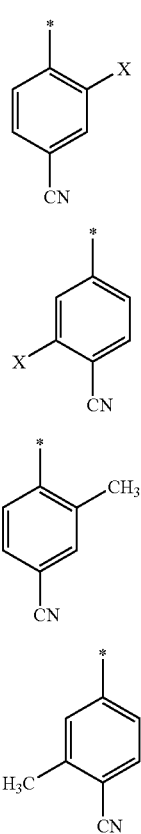

A20, B20

A21, B21

A22, B22

A23, B23

According to one embodiment, A is A1.
According to a further embodiment, A is A2 where X=F.
According to a further embodiment, A is A2 where X=Cl.
According to a preferred embodiment, A is A3 where X=F.
According to a preferred embodiment, A is A3 where X=Cl.
According to a further embodiment, A is A4 where X=F.
According to a further embodiment, A is A4 where X=CL.
According to a further embodiment, A is A5 where X=F.
According to a further embodiment, A is A5 where X=Cl.
According to a further embodiment, A is A6.
According to a further embodiment, A is A7.
According to a further embodiment, A is A8.
According to a further embodiment, A is A9.
According to a further embodiment, A is A10.
According to a further embodiment, A is A11 where X=F.
According to a further embodiment, A is A11 where X=Cl.
According to a further embodiment, A is A12 where X=F.
According to a further embodiment, A is A12 where X=Cl.
According to a further embodiment, A is A13 where X=F.
According to a further embodiment, A is A13 where X=Cl.
According to a further embodiment, A is A14 where X=F.
According to a further embodiment, A is A14 where X=Cl.
According to a further embodiment, A is A15.
According to a particularly preferred embodiment, A is A16.
According to a further embodiment, A is A17.
According to a further embodiment, A is A18.
According to a further embodiment, A is A19.
According to a further embodiment, A is A20 where X=F.
According to a further embodiment, A is A20 where X=Cl.
According to a particularly preferred embodiment, A is A21 where X=F.
According to a further embodiment, A is A21 where X=Cl.
According to a further embodiment, A is A22.
According to a further embodiment, A is A23.
According to one embodiment, B is B1.
According to a further embodiment, B is B2 where X=F.
According to a further embodiment, B is B2 where X=Cl.
According to a preferred embodiment, B is B3 where X=F.
According to a preferred embodiment, B is B3 where X=Cl.
According to a further embodiment, B is B4 where X=F.
According to a further embodiment, B is B4 where X=CL.
According to a further embodiment, B is B5 where X=F.
According to a further embodiment, B is B5 where X=Cl.
According to a further embodiment, B is B6.
According to a further embodiment, B is B7.
According to a further embodiment, B is B8.
According to a further embodiment, B is B9.
According to a further embodiment, B is B10.
According to a further embodiment, B is B11 where X=F.
According to a further embodiment, B is B11 where X=Cl.
According to a further embodiment, B is B12 where X=F.
According to a further embodiment, B is B12 where X=Cl.
According to a further embodiment, B is B13 where X=F.
According to a further embodiment, B is B13 where X=Cl.
According to a further embodiment, B is B14 where X=F.
According to a further embodiment, B is B14 where X=Cl.
According to a preferred embodiment, B is B15.
According to a particularly preferred embodiment, B is B16.
According to a further embodiment, B is B17.
According to a further embodiment, B is B18.
According to a further embodiment, B is B19.
According to a further embodiment, B is B20 where X=F.
According to a further embodiment, B is B20 where X=Cl.
According to a particularly preferred embodiment, B is B21 where X=F.
According to a further embodiment, B is B21 where X=Cl.
According to a further embodiment, B is B22.
According to a further embodiment, B is B23.

In a further embodiment of the present invention, the respective other substituent A or B is phenyl which is substituted by one to three of the following substituents: halogen, CN, $NO_2$, amino $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the respective other substituent A or B is phenyl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a preferred embodiment, the respective other substituent A or B is phenyl which is substituted by one to three halogen.

In a further embodiment, the substituent A or B is a 5-membered heteroaryl which is optionally substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the substituent A or B is a 5-membered heteroaryl selected from the group consisting of furyl, thienyl, pyrrolyl, pyrazolyl, imidazolyl, triazolyl, tetrazolyl, oxazolyl, isoxazolyl, 1,3,4-oxadiazolyl, thiazolyl, isothiazolyl and thiadiazolyl.

In a further embodiment, the substituent A or B is a 5-membered heteroaryl selected from the group consisting of furyl, thienyl, pyrrolyl, pyrazolyl, triazolyl and thiazolyl.

In a further embodiment, the substituent A or B is a 5-membered heteroaryl selected from the group consisting of thienyl, triazolyl and pyrazolyl.

In a further embodiment, the substituent A or B is a 5-membered heteroaryl which is substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the substituent A or B is a 5-membered heteroaryl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a further embodiment, the substituent A or B is a 5-membered heteroaryl which is substituted by one to three of the following substituents: halogen, $C_1$-$C_4$-alkyl or $C_1$-$C_4$-alkoxy.

In a further embodiment, the substituent A or B is a 6-membered heteroaryl which is optionally substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the substituent A or B is a 6-membered heteroaryl selected from the group consisting of pyridinyl, pyrimidinyl, pyrazinyl, pyridazinyl, 1,2,3-triazinyl, 1,2,4-triazinyl and 1,3,5-triazinyl.

In a further embodiment, the substituent A or B is a 6-membered heteroaryl selected from the group consisting of pyridyl and pyrimidinyl.

In a further embodiment, the substituent A or B is a 6-membered heteroaryl which is substituted by one to three of the following substituents: halogen, CN, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

In a further embodiment, the substituent A or B is a 6-membered heteroaryl which is substituted by one to three of the following substituents: halogen, $C_1$-$C_4$-alkyl, $C_1$-$C_4$-alkoxy, $C_1$-$C_4$-haloalkyl or $C_1$-$C_4$-haloalkoxy.

In a further embodiment, the substituent A or B is a 6-membered heteroaryl which is substituted by one to three of the following substituents: halogen, $C_1$-$C_4$-alkyl or $C_1$-$C_4$-alkoxy.

In particular with a view to their use, preference is given to the compounds I according to the invention compiled in Tables 2 to 13 below. The groups mentioned for a substituent in the tables are furthermore per se, independently of the combination in which they are mentioned, a particularly preferred embodiment of the substituent in question.

TABLE 1

| Row | Substituent B |
| --- | --- |
| 1-1 | 2-methylphenyl |
| 1-2 | 3-methylphenyl |
| 1-3 | 4-methylphenyl |
| 1-4 | 2-methoxyphenyl |
| 1-5 | 3-methoxyphenyl |
| 1-6 | 4-methoxyphenyl |
| 1-7 | 2-chlorophenyl |
| 1-8 | 3-chlorophenyl |
| 1-9 | 4-chlorophenyl |
| 1-10 | 2-fluorophenyl |
| 1-11 | 3-fluorophenyl |
| 1-12 | 4-fluorophenyl |
| 1-13 | 2-chloro-3-methoxyphenyl |
| 1-14 | 2-chloro-4-methoxyphenyl |

TABLE 1-continued

| Row | Substituent B |
| --- | --- |
| 1-15 | 2,3-dichlorophenyl |
| 1-16 | 2,4-dichlorophenyl |
| 1-17 | 3,4-dichlorophenyl |
| 1-18 | 2,3-difluorophenyl |
| 1-19 | 2,4-difluorophenyl |
| 1-20 | 2-chloro-3-fluorophenyl |
| 1-21 | 2-chloro-4-fluorophenyl |
| 1-22 | 2-pyridinyl |
| 1-23 | 3-pyridinyl |
| 1-24 | 4-pyridinyl |
| 1-25 | 2-chloropyridin-4-yl |
| 1-26 | 3-chloropyridin-4-yl |
| 1-27 | 2,6-dichloropyridin-4-yl |
| 1-28 | 3,5-dichloropyridin-4-yl |
| 1-29 | 3,6-dichloropyridin-4-yl |
| 1-30 | 2-fluoropyridin-4-yl |
| 1-31 | 3-fluoropyridin-4-yl |
| 1-32 | 2-chloropyridin-3-yl |
| 1-33 | 4-chloropyridin-3-yl |
| 1-34 | 5-chloropyridin-3-yl |
| 1-35 | 6-chloropyridin-3-yl |
| 1-36 | 2,4-dichloropyridin-3-yl |
| 1-37 | 2,5-dichloropyridin-3-yl |
| 1-38 | 2,6-dichloropyridin-3-yl |
| 1-39 | 2-fluoropyridin-3-yl |
| 1-40 | 4-fluoropyridin-3-yl |
| 1-41 | 5-fluoropyridin-3-yl |
| 1-42 | 6-fluoropyridin-3-yl |
| 1-43 | 3-chloropyridin-2-yl |
| 1-44 | 4-chloropyridin-2-yl |
| 1-45 | 5-chloropyridin-2-yl |
| 1-46 | 6-chloropyridin-2-yl |
| 1-47 | 3-fluoropyridin-2-yl |
| 1-48 | 4-fluoropyridin-2-yl |
| 1-49 | 5-fluoropyridin-2-yl |
| 1-50 | 6-fluoropyridin-2-yl |
| 1-51 | 2-methylpyridin-4-yl |
| 1-52 | 3-methylpyridin-4-yl |
| 1-53 | 2-methylpyridin-3-yl |
| 1-54 | 4-methylpyridin-3-yl |
| 1-55 | 5-methylpyridin-3-yl |
| 1-56 | 6-methylpyridin-3-yl |
| 1-57 | 3-methylpyridin-2-yl |
| 1-58 | 4-methylpyridin-2-yl |
| 1-59 | 5-methylpyridin-2-yl |
| 1-60 | 6-methylpyridin-2-yl |
| 1-61 | 2-methoxypyridin-4-yl |
| 1-62 | 3-methoxypyridin-4-yl |
| 1-63 | 2-methoxypyridin-3-yl |
| 1-64 | 4-methoxypyridin-3-yl |
| 1-65 | 5-methoxypyridin-3-yl |
| 1-66 | 6-methoxypyridin-3-yl |
| 1-67 | 3-methoxypyridin-2-yl |
| 1-68 | 4-methoxypyridin-2-yl |
| 1-69 | 5-methoxypyridin-2-yl |
| 1-70 | 6-methoxypyridin-2-yl |
| 1-71 | 6-chloropyrimidin-3-yl |
| 1-72 | 6-methylpyrimidin-3-yl |
| 1-73 | 2-pyrimidinyl |
| 1-74 | 4-pyrimidinyl |
| 1-75 | 5-pyrimidinyl |
| 1-76 | 6-methoxypyrimidin-3-yl |
| 1-77 | 2,4-dichloropyrimidin-3-yl |
| 1-78 | 2,6-dichloropyrimidin-3-yl |
| 1-79 | 2,4-difluoropyrimidin-3-yl |
| 1-80 | 2,6-difluoropyrimidin-3-yl |
| 1-81 | 2-thienyl |
| 1-82 | 3-thienyl |
| 1-83 | 2-chlorothien-3-yl |
| 1-84 | 4-chlorothien-3-yl |
| 1-85 | 5-chlorothien-3-yl |
| 1-86 | 2,5-dichlorothien-3-yl |
| 1-87 | 2,4,5-trichlorothien-3-yl |
| 1-88 | 2-bromothien-3-yl |
| 1-89 | 4-bromothien-3-yl |
| 1-90 | 5-bromothien-3-yl |
| 1-91 | 2,5-dibromothien-3-yl |
| 1-92 | 2,4,5-tribromothien-3-yl |

TABLE 1-continued

| Row | Substituent B |
|---|---|
| 1-93 | 3-pyrazolyl |
| 1-94 | 4-pyrazolyl |
| 1-95 | 1-methylpyrazol-3-yl |
| 1-96 | 1-methylpyrazol-4-yl |
| 1-97 | 1-methylpyrazol-5-yl |
| 1-98 | 2-imidazolyl |
| 1-99 | 4-imidazolyl |
| 1-100 | 1-methylimidazol-2-yl |
| 1-101 | 1-methylimidazol-4-yl |
| 1-102 | 1-methylimidazol-5-yl |
| 1-103 | 1,5-dimethylimidazol-4-yl |
| 1-104 | 1,2-dimethylimidazol-5-yl |
| 1-105 | 1,4-dimethylimidazol-5-yl |

TABLE 2

| Row | Substituent A |
|---|---|
| 2-1 | 2-methylphenyl |
| 2-2 | 3-methylphenyl |
| 2-3 | 4-methylphenyl |
| 2-4 | 2-methoxyphenyl |
| 2-5 | 3-methoxyphenyl |
| 2-6 | 4-methoxyphenyl |
| 2-7 | 2-chlorophenyl |
| 2-8 | 3-chlorophenyl |
| 2-9 | 4-chlorophenyl |
| 2-10 | 2-fluorophenyl |
| 2-11 | 3-fluorophenyl |
| 2-12 | 4-fluorophenyl |
| 2-13 | 2-chloro-3-methoxyphenyl |
| 2-14 | 2-chloro-4-methoxyphenyl |
| 2-15 | 2,3-dichlorophenyl |
| 2-16 | 2,4-dichlorophenyl |
| 2-17 | 3,4-dichlorophenyl |
| 2-18 | 2,3-difluorophenyl |
| 2-19 | 2,4-difluorophenyl |
| 2-20 | 2-chloro-3-fluorophenyl |
| 2-21 | 2-chloro-4-fluorophenyl |
| 2-22 | 2-pyridinyl |
| 2-23 | 3-pyridinyl |
| 2-24 | 4-pyridinyl |
| 2-25 | 2-chloropyridin-4-yl |
| 2-26 | 3-chloropyridin-4-yl |
| 2-27 | 2,6-dichloropyridin-4-yl |
| 2-28 | 3,5-dichloropyridin-4-yl |
| 2-29 | 3,6-dichloropyridin-4-yl |
| 2-30 | 2-fluoropyridin-4-yl |
| 2-31 | 3-fluoropyridin-4-yl |
| 2-32 | 2-chloropyridin-3-yl |
| 2-33 | 4-chloropyridin-3-yl |
| 2-34 | 5-chloropyridin-3-yl |
| 2-35 | 6-chloropyridin-3-yl |
| 2-36 | 2,4-dichloropyridin-3-yl |
| 2-37 | 2,5-dichloropyridin-3-yl |
| 2-38 | 2,6-dichloropyridin-3-yl |
| 2-39 | 2-fluoropyridin-3-yl |
| 2-40 | 4-fluoropyridin-3-yl |
| 2-41 | 5-fluoropyridin-3-yl |
| 2-42 | 6-fluoropyridin-3-yl |
| 2-43 | 3-chloropyridin-2-yl |
| 2-44 | 4-chloropyridin-2-yl |
| 2-45 | 5-chloropyridin-2-yl |
| 2-46 | 6-chloropyridin-2-yl |
| 2-47 | 3-fluoropyridin-2-yl |
| 2-48 | 4-fluoropyridin-2-yl |
| 2-49 | 5-fluoropyridin-2-yl |
| 2-50 | 6-fluoropyridin-2-yl |
| 2-51 | 2-methylpyridin-4-yl |
| 2-52 | 3-methylpyridin-4-yl |
| 2-53 | 2-methylpyridin-3-yl |
| 2-54 | 4-methylpyridin-3-yl |
| 2-55 | 5-methylpyridin-3-yl |
| 2-56 | 6-methylpyridin-3-yl |
| 2-57 | 3-methylpyridin-2-yl |

TABLE 2-continued

| Row | Substituent A |
|---|---|
| 2-58 | 4-methylpyridin-2-yl |
| 2-59 | 5-methylpyridin-2-yl |
| 2-60 | 6-methylpyridin-2-yl |
| 2-61 | 2-methoxypyridin-4-yl |
| 2-62 | 3-methoxypyridin-4-yl |
| 2-63 | 2-methoxypyridin-3-yl |
| 2-64 | 4-methoxypyridin-3-yl |
| 2-65 | 5-methoxypyridin-3-yl |
| 2-66 | 6-methoxypyridin-3-yl |
| 2-67 | 3-methoxypyridin-2-yl |
| 2-68 | 4-methoxypyridin-2-yl |
| 2-69 | 5-methoxypyridin-2-yl |
| 2-70 | 6-methoxypyridin-2-yl |
| 2-71 | 6-chloropyrimidin-3-yl |
| 2-72 | 6-methylpyrimidin-3-yl |
| 2-73 | 2-pyrimidinyl |
| 2-74 | 4-pyrimidinyl |
| 2-75 | 5-pyrimidinyl |
| 2-76 | 6-methoxypyrimidin-3-yl |
| 2-77 | 2,4-dichloropyrimidin-3-yl |
| 2-78 | 2,6-dichloropyrimidin-3-yl |
| 2-79 | 2,4-difluoropyrimidin-3-yl |
| 2-80 | 2,6-difluoropyrimidin-3-yl |
| 2-81 | 2-thienyl |
| 2-82 | 3-thienyl |
| 2-83 | 2-chlorothien-3-yl |
| 2-84 | 4-chlorothien-3-yl |
| 2-85 | 5-chlorothien-3-yl |
| 2-86 | 2,5-dichlorothien-3-yl |
| 2-87 | 2,4,5-trichlorothien-3-yl |
| 2-88 | 2-bromothien-3-yl |
| 2-89 | 4-bromothien-3-yl |
| 2-90 | 5-bromothien-3-yl |
| 2-91 | 2,5-dibromothien-3-yl |
| 2-92 | 2,4,5-tribromothien-3-yl |
| 2-93 | 3-pyrazolyl |
| 2-94 | 4-pyrazolyl |
| 2-95 | 1-methyl-pyrazol-3-yl |
| 2-96 | 1-methyl-pyrazol-4-yl |
| 2-97 | 1-methyl-pyrazol-5-yl |
| 2-98 | 2-imidazolyl |
| 2-99 | 4-imidazolyl |
| 2-100 | 1-methylimidazol-2-yl |
| 2-101 | 1-methylimidazol-4-yl |
| 2-102 | 1-methylimidazol-5-yl |
| 2-103 | 1,5-dimethylimidazol-4-yl |
| 2-104 | 1,2-dimethylimidazol-5-yl |
| 2-105 | 1,4-dimethylimidazol-5-yl |

Table 3
Compounds of the formula I in which A is A1 and B corresponds in each case to a substituent from a row of Table 1.
Table 4
Compounds of the formula I in which A is A2 where X=F and B corresponds in each case to a substituent from a row of Table 1.
Table 5
Compounds of the formula I in which A is A2 where X=Cl and B corresponds in each case to a substituent from a row of Table 1.
Table 6
Compounds of the formula I in which A is A3 where X=F and B corresponds in each case to a substituent from a row of Table 1.
Table 7
Compounds of the formula I in which A is A3 where X=Cl and B corresponds in each case to a substituent from a row of Table 1.
Table 8
Compounds of the formula I in which A is A4 where X=F and B corresponds in each case to a substituent from a row of Table 1.

Table 9
Compounds of the formula I in which A is A4 where X=Cl and B corresponds in each case to a substituent from a row of Table 1.

Table 10
Compounds of the formula I in which A is A5 where X=F and B corresponds in each case to a substituent from a row of Table 1.

Table 11
Compounds of the formula I in which A is A5 where X=Cl and B corresponds in each case to a substituent from a row of Table 1.

Table 12
Compounds of the formula I in which A is A6 and B corresponds in each case to a substituent from a row of Table 1.

Table 13
Compounds of the formula I in which A is A7 and B corresponds in each case to a substituent from a row of Table 1.

Table 14
Compounds of the formula I in which A is A8 and B corresponds in each case to a substituent from a row of Table 1.

Table 15
Compounds of the formula I in which A is A9 and B corresponds in each case to a substituent from a row of Table 1.

Table 16
Compounds of the formula I in which A is A10 and B corresponds in each case to a substituent from a row of Table 1.

Table 17
Compounds of the formula I in which A is A11 where X=F and B corresponds in each case to a substituent from a row of Table 1.

Table 18
Compounds of the formula I in which A is A11 where X=Cl and B corresponds in each case to a substituent from a row of Table 1.

Table 19
Compounds of the formula I in which A is A12 where X=F and B corresponds in each case to a substituent from a row of Table 1.

Table 20
Compounds of the formula I in which A is A12 where X=Cl and B corresponds in each case to a substituent from a row of Table 1.

Table 21
Compounds of the formula I in which A is A13 where X=F and B corresponds in each case to a substituent from a row of Table 1.

Table 22
Compounds of the formula I in which A is A13 where X=Cl and B corresponds in each case to a substituent from a row of Table 1.

Table 23
Compounds of the formula I in which A is A14 where X=F and B corresponds in each case to a substituent from a row of Table 1.

Table 24
Compounds of the formula I in which A is A14 where X=Cl and B corresponds in each case to a substituent from a row of Table 1.

Table 25
Compounds of the formula I in which A is A15 and B corresponds in each case to a substituent from a row of Table 1.

Table 26
Compounds of the formula I in which A is A16 and B corresponds in each case to a substituent from a row of Table 1.

Table 27
Compounds of the formula I in which A is A17 and B corresponds in each case to a substituent from a row of Table 1.

Table 28
Compounds of the formula I in which A is A18 and B corresponds in each case to a substituent from a row of Table 1.

Table 29
Compounds of the formula I in which A is A19 and B corresponds in each case to a substituent from a row of Table 1.

Table 30
Compounds of the formula I in which A is A20 where X=F and B corresponds in each case to a substituent from a row of Table 1.

Table 31
Compounds of the formula I in which A is A20 where X=Cl and B corresponds in each case to a substituent from a row of Table 1.

Table 32
Compounds of the formula I in which A is A21 where X=F and B corresponds in each case to a substituent from a row of Table 1.

Table 33
Compounds of the formula I in which A is A21 where X=Cl and B corresponds in each case to a substituent from a row of Table 1.

Table 34
Compounds of the formula I in which A is A22 and B corresponds in each case to a substituent from a row of Table 1.

Table 35
Compounds of the formula I in which A is A23 and B corresponds in each case to a substituent from a row of Table 1.

Table 36
Compounds of the formula I in which B is B1 and A corresponds in each case to a substituent from a row of Table 2.

Table 37
Compounds of the formula I in which B is B2 where X=F and A corresponds in each case to a substituent from a row of Table 2.

Table 38
Compounds of the formula I in which B is B2 where X=Cl and A corresponds in each case to a substituent from a row of Table 2.

Table 39
Compounds of the formula I in which B is B3 where X=F and A corresponds in each case to a substituent from a row of Table 2.

Table 40
Compounds of the formula I in which B is B3 where X=Cl and A corresponds in each case to a substituent from a row of Table 2.

Table 41
Compounds of the formula I in which B is B4 where X=F and A corresponds in each case to a substituent from a row of Table 2.

Table 42
Compounds of the formula I in which B is B4 where X=Cl and A corresponds in each case to a substituent from a row of Table 2.

Table 43
Compounds of the formula I in which B is B5 where X=F and A corresponds in each case to a substituent from a row of Table 2.

Table 44
Compounds of the formula I in which B is B5 where X=Cl and A corresponds in each case to a substituent from a row of Table 2.

Table 45
Compounds of the formula I in which B is B6 and A corresponds in each case to a substituent from a row of Table 2.

Table 46
Compounds of the formula I in which B is B7 and A corresponds in each case to a substituent from a row of Table 2.

Table 47
Compounds of the formula I in which B is B8 and A corresponds in each case to a substituent from a row of Table 2.

Table 48
Compounds of the formula I in which B is B9 and A corresponds in each case to a substituent from a row of Table 2.

Table 49
Compounds of the formula I in which B is B10 and A corresponds in each case to a substituent from a row of Table 2.

Table 50
Compounds of the formula I in which B is B11 where X=F and A corresponds in each case to a substituent from a row of Table 2.

Table 51
Compounds of the formula I in which B is B11 where X=Cl and A corresponds in each case to a substituent from a row of Table 2.

Table 52
Compounds of the formula I in which B is B12 where X=F and A corresponds in each case to a substituent from a row of Table 2.

Table 53
Compounds of the formula I in which B is B12 where X=Cl and A corresponds in each case to a substituent from a row of Table 2.

Table 54
Compounds of the formula I in which B is B13 where X=F and A corresponds in each case to a substituent from a row of Table 2.

Table 55
Compounds of the formula I in which B is B13 where X=Cl and A corresponds in each case to a substituent from a row of Table 2.

Table 56
Compounds of the formula I in which B is B14 where X=F and A corresponds in each case to a substituent from a row of Table 2.

Table 57
Compounds of the formula I in which B is B14 where X=Cl and A corresponds in each case to a substituent from a row of Table 2.

Table 58
Compounds of the formula I in which B is B15 and A corresponds in each case to a substituent from a row of Table 2.

Table 59
Compounds of the formula I in which B is B16 and A corresponds in each case to a substituent from a row of Table 2.

Table 60
Compounds of the formula I in which B is B17 and A corresponds in each case to a substituent from a row of Table 2.

Table 61
Compounds of the formula I in which B is B18 and B corresponds in each case to a substituent from a row of Table 1.

Table 62
Compounds of the formula I in which B is B19 and A corresponds in each case to a substituent from a row of Table 2.

Table 63
Compounds of the formula I in which B is B20 where X=F and A corresponds in each case to a substituent from a row of Table 2.

Table 64
Compounds of the formula I in which B is B20 where X=Cl and A corresponds in each case to a substituent from a row of Table 2.

Table 65
Compounds of the formula I in which B is B21 where X=F and A corresponds in each case to a substituent from a row of Table 2.

Table 66
Compounds of the formula I in which B is B21 where X=Cl and A corresponds in each case to a substituent from a row of Table 2.

Table 67
Compounds of the formula I in which B is B22 and A corresponds in each case to a substituent from a row of Table 2.

Table 68
Compounds of the formula I in which B is B23 and A corresponds in each case to a substituent from a row of Table 2.

The compounds I are suitable as fungicides. They are distinguished by an excellent activity against a broad spectrum of phytopathogenic fungi from the class of the Ascomycetes, Deuteromycetes, Oomycetes and Basidiomycetes, in particular from the class of the Oomycetes. Some of them are systemically effective and can be used in crop protection as foliar fungicides, as fungicides for seed dressing and as soil fungicides.

They are particularly important in the control of a multitude of fungi on various crop plants, such as wheat, rye, barley, oats, rice, corn, grass, bananas, cotton, soya, coffee, sugar cane, vines, fruit and ornamental plants, and vegetable plants, such as cucumbers, beans, tomatoes, potatoes and cucurbits, and on the seeds of these plants.

They are especially suitable for controlling the following plant diseases:

*Alternaria* species on vegetables, oilseed rape, sugar beet and fruit and rice, such as, for example, *A. solani* or *A. alternata* on potatoes and tomatoes;

*Aphanomyces* species on sugar beet and vegetables;
*Ascochyta* species on cereals and vegetables;
*Bipolaris* and *Drechslera* species on corn, cereals, rice and lawns, such as, for example, *D. maydis* on corn;
*Blumeria graminis* (powdery mildew) on cereals;
*Botrytis cinerea* (gray mold) on strawberries, vegetables, flowers and grapevines;
*Bremia lactucae* on lettuce;
*Cercospora* species on corn, soybeans, rice and sugar beet;
*Cochliobolus* species on corn, cereals, rice, such as, for example, *Cochliobolus sativus* on cereals, *Cochliobolus miyabeanus* on rice;
*Colletotricum* species on soybeans and cotton;
*Drechslera* species, *Pyrenophora* species on corn, cereals, rice and lawns, such as, for example, *D. teres* on barley or *D. tritici-repentis* on wheat;
Esca on grapevines, caused by *Phaeoacremonium chlamydosporium*, *Ph. Aleophilum* and *Formitipora punctata* (syn. *Phellinus punctatus*);
*Exserohilum* species on corn;
*Erysiphe cichoracearum* and *Sphaerotheca fuliginea* on cucumber plants;
*Fusarium* and *Verticillium* species on various plants, such as, for example, *F. graminearum* or *F. culmorum* on cereals or *F. oxysporum* on a multitude of plants, such as, for example, tomatoes;
*Gaeumanomyces graminis* on cereals;
*Gibberella* species on cereals and rice (for example *Gibberella fujikuroi* on rice);
Grainstaining complex on rice;
*Helminthosporium* species on corn and rice;
*Michrodochium nivale* on cereals;
*Mycosphaerella* species on cereals, bananas and groundnuts, such as, for example, *M. graminicola* on wheat or *M. fijiensis* on bananas;
*Peronospora* species on cabbage and bulbous plants, such as, for example, *P. brassicae* on cabbage or *P. destructor* on onion;
*Phakopsara pachyrhizi* and *Phakopsara meibomiae* on soybeans;
*Phomopsis* species on soybeans and sunflowers;
*Phytophthora infestans* on potatoes and tomatoes;
*Phytophthora* species on various plants, such as, for example, *P. capsici* on bell pepper;
*Plasmopara viticola* on grapevines;
*Podosphaera leucotricha* on apple;
*Pseudocercosporella herpotrichoides* on cereals;
*Pseudoperonospora* on various plants, such as, for example, *P. cubensis* on cucumber or *P. humili* on hops;
*Puccinia* species on various plants, such as, for example, *P. triticina*, *P. striformins*, *P. hordei* or *P. graminis* on cereals or *P. asparagi* on asparagus;
*Pyricularia oryzae*, *Corticium sasakii*, *Sarocladium oryzae*, *S. attenuatum*, *Entyloma oryzae* on rice;
*Pyricularia grisea* on lawns and cereals;
*Pythium* spp. on lawns, rice, corn, cotton, oilseed rape, sunflowers, sugar beet, vegetables and other plants, such as, for example, *P. ultiumum* on various plants, *P. aphanidermatum* on lawns;
*Rhizoctonia* species on cotton, rice, potatoes, lawns, corn, oilseed rape, potatoes, sugar beet, vegetables and on various plants, such as, for example, *R. solani* on beet and various plants;
*Rhynchosporium secalis* on barley, rye and triticale;
*Sclerotinia* species on oilseed rape and sunflowers;
*Septoria tritici* and *Stagonospora nodorum* on wheat;
*Erysiphe* (syn. *Uncinula*) *necator* on grapevines;
*Setospaeria* species on corn and lawns;
*Sphacelotheca reilinia* on corn;
*Thievaliopsis* species on soybeans and cotton;
*Tilletia* species on cereals;
*Ustilago* species on cereals, corn and sugar cane, such as, for example, *U. maydis* on corn;
*Venturia* species (scab) on apples and pears, such as, for example, *V. inaequalis* on apple.

They are particularly suitable for controlling harmful fungi from the class of the Peronosporomycetes (syn. Oomycetes), such as *Peronospora* species, *Phytophthora* species, *Plasmopara viticola*, *Pseudoperonospora* species and *Pythium* species.

The compounds I are also suitable for controlling harmful fungi in the protection of materials (for example wood, paper, paint dispersions, fibers or fabrics) and in the protection of stored products. In the protection of wood, particular attention is paid to the following harmful fungi: Ascomycetes, such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., additionally in the protection of materials the following yeasts: *Candida* spp. and *Saccharomyces cerevisae*.

The compounds I are employed by treating the fungi or the plants, seeds or materials to be protected against fungal attack or the soil with a fungicidally effective amount of the active compounds. Application can be both before and after the infection of the materials, plants or seeds by the fungi.

The fungicidal compositions generally comprise between 0.1 and 95% by weight, preferably between 0.5 and 90% by weight, of active compound.

When employed in crop protection, the application rates are, depending on the kind of effect desired, between 0.01 and 2.0 kg of active compound per ha.

In seed treatment, the amounts of active compound required are generally from 1 to 1000 g/100 kg of seed, preferably from 5 to 100 g/100 kg of seed.

When used in the protection of materials or stored products, the active compound application rates depend on the kind of application area and on the desired effect. Amounts typically applied in the protection of materials are, for example, from 0.001 g to 2 kg, preferably from 0.005 g to 1 kg, of active compound per cubic meter of treated material.

The compounds of the formula I can be present in different crystal modifications which may differ in their biological activity. They are likewise subject matter of the present invention.

The compounds I can be converted into the customary formulations, for example solutions, emulsions, suspensions, dusts, powders, pastes and granules. The application form depends on the particular purpose; in each case, it should ensure a fine and uniform distribution of the compound according to the invention.

The formulations are prepared in a known manner, for example by extending the active compound with solvents and/or carriers, if desired using emulsifiers and dispersants. Solvents/auxiliaries suitable for this purpose are essentially:
water, aromatic solvents (for example Solvesso products, xylene), paraffins (for example mineral oil fractions), alcohols (for example methanol, butanol, pentanol, benzyl alcohol), ketones (for example cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used, carriers such as ground natural minerals (for example kaolins, clays, talc, chalk) and ground synthetic minerals (for example finely divided silica, silicates); emulsifiers such as nonionogenic and anionic emulsifiers (for example polyoxyethylene fatty alcohol ethers, alkylsulfonates and arylsulfonates) and dispersants such as lignosulfite waste liquors and methylcellulose.

Suitable for use as surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active compound. The active compounds are employed in a purity of from 90% to 100%, preferably 95% to 100% (according to NMR spectrum).

The following are examples of formulations: 1. Products for dilution with water

A Water-Soluble Concentrates (SL, LS)

10 parts by weight of the active compounds are dissolved with 90 parts by weight of water or with a water-soluble solvent. As an alternative, wetters or other auxiliaries are added. The active compound dissolves upon dilution with water. This gives a formulation having an active compound content of 10% by weight.

B Dispersible Concentrates (DC)

20 parts by weight of the active compounds are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates (EC)

15 parts by weight of the active compounds are dissolved in 75 parts by weight of xylene with addition of calcium dodecylbenzenesulfonate and castor oil ethoxylate (in each case 5 parts by weight). Dilution with water gives an emulsion. The formulation has an active compound content of 15% by weight.

D Emulsions (EW, EO, ES)

25 parts by weight of the active compounds are dissolved in 35 parts by weight of xylene with addition of calcium dodecylbenzenesulfonate and castor oil ethoxylate (in each case 5 parts by weight). This mixture is added to 30 parts by weight of water by means of an emulsifying machine (e.g. Ultraturrax) and made into a homogeneous emulsion. Dilution with water gives an emulsion. The formulation has an active compound content of 25% by weight.

E Suspensions (SC, OD, FS)

In an agitated ball mill, 20 parts by weight of the active compounds are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules (WG, SG)

50 parts by weight of the active compounds are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders (WP, SP, SS, WS)

75 parts by weight of the active compounds are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations (GF)

20 parts by weight of the active compounds, 10 parts by weight of dispersant, 1 part by weight of gelling agent and 70 parts by weight of water or an organic solvent are ground in a ball mill to give a fine suspension. Dilution with water gives a stable suspension with an active compound content of 20% by weight.

2. Products to be Applied Undiluted

I Dusts (DP, DS)

5 parts by weight of the active compounds are ground finely and mixed intimately with 95 parts by weight of finely divided kaolin. This gives a dustable product with an active compound content of 5% by weight.

J Granules (GR, FG, GG, MG)

0.5 part by weight of the active compounds is ground finely and associated with 99.5 parts by weight of carriers. Current methods are extrusion, spray-drying or the fluidized bed. This gives granules with an active compound content of 0.5% by weight to be applied undiluted.

K ULV Solutions (UL)

10 parts by weight of the active compounds are dissolved in 90 parts by weight of an organic solvent, for example xylene. This gives a product with an active compound content of 10% by weight to be applied undiluted.

Water-soluble concentrates (LS), suspensions (FS), dusts (DS), water-dispersible and water-soluble powders (WS, SS), emulsions (ES), emulsifiable concentrates (EC) and gel formulations (GF) are usually used for the treatment of seed. These formulations can be applied to the seed in undiluted or, preferably, diluted form. The application can be carried out before sowing.

The active compounds can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; the intention is to ensure in each case the finest possible distribution of the active compounds according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active compound concentrations in the ready-to-use preparations can be varied within relatively wide ranges. In general, they are from 0.0001 to 10%, preferably from 0.01 to 1%.

The active compounds may also be used successfully in the ultra-low-volume process (ULV), by which it is possible to apply formulations comprising over 95% by weight of active compound, or even to apply the active compound without additives.

Various types of oils, wetters, adjuvants, herbicides, fungicides, other pesticides, or bactericides may be added to the active compounds, if appropriate not until immediately prior to use (tank mix). These compositions can be admixed with the compositions according to the invention in a weight ratio of from 1:100 to 100:1, preferably from 1:10 to 10:1.

The following are particularly suitable as adjuvants in this context: organically modified polysiloxanes, for example Break Thru S 240®; alcohol alkoxylates, for example Atplus 245®, Atplus MBA 1303®, Plurafac LF 300® and Lutensol ON 30®; EO-PO block polymers, for example Pluronic RPE 2035® and Genapol B®; alcohol ethoxylates, for example Lutensol XP 80®; and sodium dioctylsulfosuccinate, for example Leophen RA®.

The compositions according to the invention in the application form as fungicides can also be present together with other active compounds, for example with herbicides, insecticides, growth regulators, fungicides or else with fertilizers. When mixing the compounds I or the compositions comprising them with one or more further active compounds, in particular fungicides, it is in many cases possible, for example, to widen the activity spectrum or to prevent the development of resistance. In many cases, synergistic effects are obtained.

The present invention furthermore provides a combination of at least one azolylmethyloxirane of the formula I, in particular an azolylmethyloxirane disclosed in the present description as being preferred, and/or an agriculturally acceptable salt thereof and at least one further fungicidal, insecticidal, herbicidal and/or growth-regulating active compound, it being possible for a synergistic effect to occur.

The present invention also provides a pesticidal composition which comprises at least one compound of the formula I, in particular a compound of the formula I described in the present description as being preferred, and/or an agriculturally acceptable acid addition salt or metal salt thereof and at least one solid or liquid carrier. Such a pesticidal composition may comprise at least one further fungicidally, insecticidally and/or herbicidally active compound, it also being possible for a synergistic effect to occur.

The following list L of fungicides with which the compounds according to the invention can be applied together is meant to illustrate the possible combinations, but not to limit them:

List L:
strobilurins
azoxystrobin, dimoxystrobin, enestroburin, fluoxastrobin, kresoxim-methyl, methominostrobin, orysastrobin, picoxystrobin, pyraclostrobin, pyribencarb, trifloxystrobin, 2-(2-(6-(3-chloro-2-methylphenoxy)-5-fluoropyrimidin-4-yloxy)phenyl)-2-methoxyimino-N-methylacetamide, methyl 2-(ortho-((2,5-dimethylphenyl-oxymethylene)phenyl)-3-methoxyacrylate, methyl 3-methoxy-2-(2-(N-(4-methoxyphenyl)cyclopropanecarboximidoylsulfanylmethyl)phenyl)acrylate;

carboxamides
carboxanilides: benalaxyl, benalaxyl-M, benodanil, bixafen, boscalid, carboxin, fenfuram, fenhexamid, flutolanil, furametpyr, isotianil, kiralaxyl, mepronil, metalaxyl, ofurace, oxadixyl, oxycarboxin, penthiopyrad, tecloftalam, thifluzamide, tiadinil, 2-amino-4-methylthiazole-5-carboxanilide, 2-chloro-N-(1,1,3-trimethylindan-4-yl)-nicotinamide, N-(3',4'-dichloro-5-fluorobiphenyl-2-yl)-3-difluoromethyl-1-methyl-1H-pyrazole-4-carboxamide, N-[2-(1,3-dimethylbutyl)phenyl]-5-fluoro-1,3-dimethyl-1H-pyrazole-4-carboxamide, N-(4'-chloro-3',5-difluorobiphenyl-2-yl)-3-difluoromethyl-1-methyl-1H-pyrazole-4-carboxamide, N-(4'-chloro-3',5-difluorobiphenyl-2-yl)-3-trifluoromethyl-1-methyl-1H-pyrazole-4-carboxamide, N-(3',4'-dichloro-5-fluorobiphenyl-2-yl)-3-trifluoromethyl-1-methyl-1H-pyrazole-4-carboxamide, N-(3',5-difluoro-4'-methylbiphenyl-2-yl)-3-difluoromethyl-1-methyl-1H-pyrazole-4-carboxamide, N-(3',5-difluoro-4'-methylbiphenyl-2-yl)-3-trifluoromethyl-1-methyl-1H-pyrazole-4-carboxamide, N-(2-bicyclopropyl-2-ylphenyl)-3-difluoromethyl-1-methyl-1H-pyrazole-4-carboxamide, N-(cis-2-bicyclopropyl-2-ylphenyl)-3-difluoromethyl-1-methyl-1H-pyrazole-4-carboxamide, N-(trans-2-bicyclopropyl-2-ylphenyl)-3-difluoromethyl-1-methyl-1H-pyrazole-4-carboxamide,
carboxylic acid morpholides: dimethomorph, flumorph;
benzamides: flumetover, fluopicolide, fluopyram, zoxamide, N-(3-ethyl-3,5,5-trimethylcyclohexyl)-3-formylamino-2-hydroxybenzamide;
other carboxamides: carpropamid, diclocymet, mandipropamid, oxytetracyclin, silthiofam, N-(6-methoxypyridin-3-yl)cyclopropanecarboxamide;

azoles triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-(4-chlorophenyl)-2-([1,2,4]triazol-1-yl)-cycloheptanol;

imidazoles: cyazofamid, imazalil, imazalil-sulfate, pefurazoate, prochloraz, triflumizole;

benzimidazoles: benomyl, carbendazim, fuberidazole, thiabendazole;

others: ethaboxam, etridiazole, hymexazole, 1-(4-chlorophenyl)-1-(propyn-2-yloxy)-3-(4-(3,4-dimethoxyphenyl)isoxazol-5-yl)propan-2-one;

nitrogenous heterocyclyl compounds pyridines: fluazinam, pyrifenox, 3-[5-(4-chlorophenyl)-2,3-dimethylisoxazolidin-3-yl]-pyridine, 2,3,5,6-tetrachloro-4-methanesulfonylpyridine, 3,4,5-trichloropyridine-2,6-dicarbonitrile, N-(1-(5-bromo-3-chloropyridin-2-yl)ethyl)-2,4-dichloronicotinamide, N-((5-bromo-3-chloropyridin-2-yl)methyl)-2,4-dichloronicotinamide;

pyrimidines: bupirimate, cyprodinil, diflumetorim, fenarimol, ferimzone, mepanipyrim, nitrapyrin, nuarimol, pyrimethanil;

pyrroles: fludioxonil, fenpiclonil;

morpholines: aldimorph, dodemorph, dodemorph-acetate, fenpropimorph, tridemorph;

dicarboximides: fluoroimide, iprodione, procymidone, vinclozolin;

others: acibenzolar-S-methyl, amisulbrom, anilazine, blasticidin-S, captafol, captan, quinomethionate, dazomet, debacarb, diclomezine, difenzoquat, difenzoquat-methyl sulfate, famoxadone, fenamidone, fenoxanil, fenpropidin, folpet, octhilinone, oxolinic acid, piperalin, probenazole, proquinazid, pyroquilon, quinoxyfen, triazoxide, tricyclazole, triforine, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one;

carbamates and dithiocarbamates thio- and dithiocarbamates: ferbam, mancozeb, maneb, metam, methasulfocarb, metiram, propineb, thiram, zineb, ziram;

carbamates: diethofencarb, benthiavalicarb, iprovalicarb, propamocarb, propamocarb hydrochloride, valiphenal, (4-fluorophenyl) N-(1-(1-(4-cyanophenyl)-ethanesulfonyl)but-2-yl)carbamate;

other fungicides guanidines: dodine, dodine-free base, guazatine, guazatine-acetate, iminoctadine, iminoctadine-triacetate, iminoctadine-tris(albesilate);

antibiotics: kasugamycin, kasugamycin-hydrochloride-hydrate, polyoxins, streptomycin, validamycin A;

nitrophenyl derivatives:

binapacryl, dicloran, dinobuton, dinocap, nitrothal-isopropyl, tecnazen;

organometallic compounds: fentin salts such as, for example, fentin-acetate, fentinchloride, fentin-hydroxide;

sulfur-containing heterocyclyl compounds: isoprothiolane, dithianon;

organophosphorus compounds: edifenphos, fosetyl, fosetyl-aluminum, iprobenfos, pyrazophos, tolclofos-methyl;

organochlorine compounds: chlorothalonil, dichlofluanid, dichlorophen, flusulfamide, hexachlorobenzene, pencycuron, pentachlorophenol and salts thereof, phthalide, quintozene, thiophanate-methyl, tolylfluanid, N-(4-chloro-2-nitrophenyl)-N-ethyl-4-methylbenzenesulfonamide;

inorganic active compounds: phosphorous acid and salts thereof, sulfur, Bordeaux mixture, copper salts such as, for example, copper acetate, copper hydroxide, copper oxychloride, basic copper sulfate;

others: biphenyl, bronopol, cyflufenamid, cymoxanil, diphenylamin, metrafenone, mildiomycin, oxine-copper, prohexadione-calcium, spiroxamine, tolylfluanid, N-(cyclopropylmethoxyimino-(6-difluoromethoxy-2,3-difluorophenyl)methyl)-2-phenyl acetamide, N'-(4-(4-chloro-3-trifluoromethylphenoxy)-2,5-dimethylphenyl)-N-ethyl-N-methylformamidine, N'-(4-(4-fluoro-3-trifluoromethylphenoxy)-2,5-dimethylphenyl)-N-ethyl-N-methylformamidine, N'-(2-methyl-5-trifluoromethyl-4-(3-trimethylsilanylpropoxy)phenyl)-N-ethyl-N-methylformamidine, N'-(5-difluoromethyl-2-methyl-4-(3-trimethylsilanylpropoxy)phenyl)-N-ethyl-N-methylformamidine.

The present invention further relates, accordingly, to the compositions that are listed in table B, each line of table B corresponding to a fungicidal composition comprising a compound of the formula I (component 1), which is preferably one of the compounds described herein as being preferred, and comprising the further active compound indicated in each case in the line in question (component 2). According to one embodiment of the invention, component 1 in each line of table B is in each case one of the compounds of the formula I that are specifically individualized in tables 1 to 68.

TABLE B

| Line | Component 1 | Component 2 |
| --- | --- | --- |
| B-1 | a compound of the formula I | azoxystrobin |
| B-2 | a compound of the formula I | dimoxystrobin |
| B-3 | a compound of the formula I | enestroburin |
| B-4 | a compound of the formula I | fluoxastrobin |
| B-5 | a compound of the formula I | kresoxim-methyl |
| B-6 | a compound of the formula I | metominostrobin |
| B-7 | a compound of the formula I | orysastrobin |
| B-8 | a compound of the formula I | picoxystrobin |
| B-9 | a compound of the formula I | pyraclostrobin |
| B-10 | a compound of the formula I | pyribencarb |
| B-11 | a compound of the formula I | trifloxystrobin |

TABLE B-continued

| Line | Component 1 | Component 2 |
|---|---|---|
| B-12 | a compound of the formula I | 2-(2-(6-(3-chloro-2-methylphenoxy)-5-fluoropyrimidin-4-yloxy)phenyl)-2-methoxyimino-N-methylacetamide |
| B-13 | a compound of the formula I | 2-(ortho-((2,5-dimethylphenyloxy-methylene)phenyl)-3-methoxyacrylic acid methyl ester |
| B-14 | a compound of the formula I | 3-methoxy-2-(2-(N-(4-methoxyphenyl)-cyclopropanecarboximidoylsulfanyl-methyl)phenyl)acrylic acid methyl ester |
| B-15 | a compound of the formula I | benalaxyl |
| B-16 | a compound of the formula I | benalaxyl-M |
| B-17 | a compound of the formula I | benodanil |
| B-18 | a compound of the formula I | bixafen |
| B-19 | a compound of the formula I | boscalid |
| B-20 | a compound of the formula I | carboxin |
| B-21 | a compound of the formula I | fenfuram |
| B-22 | a compound of the formula I | fenhexamid |
| B-23 | a compound of the formula I | flutolanil |
| B-24 | a compound of the formula I | furametpyr |
| B-25 | a compound of the formula I | isotianil |
| B-26 | a compound of the formula I | kiralaxyl |
| B-27 | a compound of the formula I | mepronil |
| B-28 | a compound of the formula I | metalaxyl |
| B-29 | a compound of the formula I | ofurace |
| B-30 | a compound of the formula I | oxadixyl |
| B-31 | a compound of the formula I | oxycarboxin |
| B-32 | a compound of the formula I | penthiopyrad |
| B-33 | a compound of the formula I | thifluzamide |
| B-34 | a compound of the formula I | tecloftalam |
| B-35 | a compound of the formula I | tiadinil |
| B-36 | a compound of the formula I | 2-amino-4-methylthiazole-5-carboxanilide |
| B-37 | a compound of the formula I | 2-chloro-N-(1,1,3-trimethylindan-4-yl)-nicotinamide |
| B-38 | a compound of the formula I | N-(3',4'-dichloro-5-fluorobiphenyl-2-yl)-3-difluoromethyl-1-methyl-1H-pyrazole-4-carboxamide |
| B-39 | a compound of the formula I | 5-fluoro-1,3-dimethyl-1H-pyrazole-4-carboxylic acid [2-(1,3-dimethylbutyl)-phenyl]amide |
| B-40 | a compound of the formula I | N-(4'-chloro-3',5-difluorobiphenyl-2-yl)-3-difluoromethyl-1-methyl-1H-pyrazole-4-carboxamide |
| B-41 | a compound of the formula I | N-(4'-chloro-3',5-difluorobiphenyl-2-yl)-3-trifluoromethyl-1-methyl-1H-pyrazole-4-carboxamide |
| B-42 | a compound of the formula I | N-(3',4'-dichloro-5-fluorobiphenyl-2-yl)-3-trifluoromethyl-1-methyl-1H-pyrazole-4-carboxamide |
| B-43 | a compound of the formula I | N-(3',5-difluoro-4'-methylbiphenyl-2-yl)-3-difluoromethyl-1-methyl-1H-pyrazole-4-carboxamide |
| B-44 | a compound of the formula I | N-(3',5-difluoro-4'-methylbiphenyl-2-yl)-3-trifluoromethyl-1-methyl-1H-pyrazole-4-carboxamide |
| B-45 | a compound of the formula I | N-(2-bicyclopropyl-2-yl-phenyl)-3-difluoro-methyl-1-methyl-1H-pyrazole-4-carboxamide |
| B-46 | a compound of the formula I | N-(cis-2-bicyclopropyl-2-yl-phenyl)-3-difluoromethyl-1-methyl-1H-pyrazole-4-carboxamide |
| B-47 | a compound of the formula I | N-(trans-2-bicyclopropyl-2-yl-phenyl)-3-difluoromethyl-1-methyl-1H-pyrazole-4-carboxamide |
| B-48 | a compound of the formula I | dimethomorph |
| B-49 | a compound of the formula I | flumorph |
| B-50 | a compound of the formula I | flumetover |
| B-51 | a compound of the formula I | fluopicolide (picobenzamid) |
| B-52 | a compound of the formula I | fluopyram |
| B-53 | a compound of the formula I | zoxamide |
| B-54 | a compound of the formula I | N-(3-ethyl-3,5,5-trimethylcyclohexyl)-3-formylamino-2-hydroxybenzamide |
| B-55 | a compound of the formula I | carpropamid |
| B-56 | a compound of the formula I | diclocymet |
| B-57 | a compound of the formula I | mandipropamid |
| B-58 | a compound of the formula I | oxytetracyclin |
| B-59 | a compound of the formula I | silthiofam |
| B-60 | a compound of the formula I | N-(6-methoxypyridin-3-yl)cyclopropane-carboxamide |

TABLE B-continued

| Line | Component 1 | Component 2 |
|---|---|---|
| B-61 | a compound of the formula I | azaconazole |
| B-62 | a compound of the formula I | bitertanol |
| B-63 | a compound of the formula I | bromuconazole |
| B-64 | a compound of the formula I | cyproconazole |
| B-65 | a compound of the formula I | difenoconazole |
| B-66 | a compound of the formula I | diniconazole |
| B-67 | a compound of the formula I | diniconazole-M |
| B-68 | a compound of the formula I | enilconazole |
| B-69 | a compound of the formula I | epoxiconazole |
| B-70 | a compound of the formula I | fenbuconazole |
| B-71 | a compound of the formula I | flusilazole |
| B-72 | a compound of the formula I | fluquinconazole |
| B-73 | a compound of the formula I | flutriafol |
| B-74 | a compound of the formula I | hexaconazol |
| B-75 | a compound of the formula I | imibenconazole |
| B-76 | a compound of the formula I | ipconazole |
| B-77 | a compound of the formula I | metconazol |
| B-78 | a compound of the formula I | myclobutanil |
| B-79 | a compound of the formula I | oxpoconazol |
| B-80 | a compound of the formula I | paclobutrazol |
| B-81 | a compound of the formula I | penconazole |
| B-82 | a compound of the formula I | propiconazole |
| B-83 | a compound of the formula I | prothioconazole |
| B-84 | a compound of the formula I | simeconazole |
| B-85 | a compound of the formula I | tebuconazole |
| B-86 | a compound of the formula I | tetraconazole |
| B-87 | a compound of the formula I | triadimenol |
| B-88 | a compound of the formula I | triadimefon |
| B-89 | a compound of the formula I | triticonazole |
| B-90 | a compound of the formula I | uniconazol |
| B-91 | a compound of the formula I | 1-(4-chlorophenyl)-2-([1,2,4]triazol-1-yl)-cycloheptanol |
| B-92 | a compound of the formula I | cyazofamid |
| B-93 | a compound of the formula I | imazalil |
| B-94 | a compound of the formula I | imazalil-sulfate |
| B-95 | a compound of the formula I | pefurazoate |
| B-96 | a compound of the formula I | prochloraz |
| B-97 | a compound of the formula I | triflumizole |
| B-98 | a compound of the formula I | benomyl |
| B-99 | a compound of the formula I | carbendazim |
| B-100 | a compound of the formula I | fuberidazole |
| B-101 | a compound of the formula I | thiabendazole |
| B-102 | a compound of the formula I | ethaboxam |
| B-103 | a compound of the formula I | etridiazole |
| B-104 | a compound of the formula I | hymexazole |
| B-105 | a compound of the formula I | fluazinam |
| B-106 | a compound of the formula I | pyrifenox |
| B-107 | a compound of the formula I | 1-(4-chlorophenyl)-1-(propyn-2-yloxy)-3-(4-(3,4-dimethoxyphenyl)isoxazol-5-yl)-propan-2-one |
| B-108 | a compound of the formula I | 3-[5-(4-chlorophenyl)-2,3-dimethyl-isoxazolidin-3-yl]pyridine |
| B-109 | a compound of the formula I | 2,3,5,6-tetrachloro-4-methanesulfonyl-pyridine |
| B-110 | a compound of the formula I | 3,4,5-trichloropyridine-2,6-dicarbonitrile |
| B-111 | a compound of the formula I | N-(1-(5-bromo-3-chloropyridin-2-yl)ethyl)-2,4-dichloronicotinamide |
| B-112 | a compound of the formula I | N-((5-bromo-3-chloropyridin-2-yl)methyl)-2,4-dichloronicotinamide |
| B-113 | a compound of the formula I | bupirimate |
| B-114 | a compound of the formula I | cyprodinil |
| B-115 | a compound of the formula I | diflumetorim |
| B-116 | a compound of the formula I | ferimzone |
| B-117 | a compound of the formula I | fenarimol |
| B-118 | a compound of the formula I | mepanipyrim |
| B-119 | a compound of the formula I | nitrapyrin |
| B-120 | a compound of the formula I | nuarimol |
| B-121 | a compound of the formula I | pyrimethanil |
| B-122 | a compound of the formula I | fludioxonil |
| B-123 | a compound of the formula I | fenpiclonil |
| B-124 | a compound of the formula I | aldimorph |
| B-125 | a compound of the formula I | dodemorph |
| B-126 | a compound of the formula I | dodemorph acetate |
| B-127 | a compound of the formula I | fenpropimorph |
| B-128 | a compound of the formula I | tridemorph |
| B-129 | a compound of the formula I | fluoroimid |
| B-130 | a compound of the formula I | iprodione |

TABLE B-continued

| Line | Component 1 | Component 2 |
|---|---|---|
| B-131 | a compound of the formula I | procymidone |
| B-132 | a compound of the formula I | vinclozolin |
| B-133 | a compound of the formula I | acibenzolar-S-methyl |
| B-134 | a compound of the formula I | amisulbrom |
| B-135 | a compound of the formula I | anilazin |
| B-136 | a compound of the formula I | blasticidin-S |
| B-137 | a compound of the formula I | captan |
| B-138 | a compound of the formula I | captafol |
| B-139 | a compound of the formula I | chinomethionat |
| B-140 | a compound of the formula I | dazomet |
| B-141 | a compound of the formula I | debacarb |
| B-142 | a compound of the formula I | diclomezine |
| B-143 | a compound of the formula I | difenzoquat |
| B-144 | a compound of the formula I | difenzoquat methylsulfate |
| B-145 | a compound of the formula I | famoxadone |
| B-146 | a compound of the formula I | fenamidone |
| B-147 | a compound of the formula I | fenoxanil |
| B-148 | a compound of the formula I | fenpropidin |
| B-149 | a compound of the formula I | folpet |
| B-150 | a compound of the formula I | octhilinone |
| B-151 | a compound of the formula I | oxolinic acid |
| B-152 | a compound of the formula I | piperalin |
| B-153 | a compound of the formula I | probenazole |
| B-154 | a compound of the formula I | proquinazid |
| B-155 | a compound of the formula I | pyroquilon |
| B-156 | a compound of the formula I | quinoxyfen |
| B-157 | a compound of the formula I | triazoxid |
| B-158 | a compound of the formula I | tricyclazole |
| B-159 | a compound of the formula I | triforine |
| B-160 | a compound of the formula I | 5-chloro-7-(4-methylpiperidin-1-yl)-6-(2,4,6-trifluorophenyl)-[1,2,4]triazolo-[1,5-a]pyrimidine |
| B-161 | a compound of the formula I | 2-butoxy-6-iodo-3-propylchromen-4-one |
| B-162 | a compound of the formula I | ferbam |
| B-163 | a compound of the formula I | mancozeb |
| B-164 | a compound of the formula I | maneb |
| B-165 | a compound of the formula I | metiram |
| B-166 | a compound of the formula I | metam |
| B-167 | a compound of the formula I | methasulphocarb |
| B-168 | a compound of the formula I | propineb |
| B-169 | a compound of the formula I | thiram |
| B-170 | a compound of the formula I | zineb |
| B-171 | a compound of the formula I | ziram |
| B-172 | a compound of the formula I | diethofencarb |
| B-173 | a compound of the formula I | flubenthiavalicarb |
| B-174 | a compound of the formula I | iprovalicarb |
| B-175 | a compound of the formula I | propamocarb |
| B-176 | a compound of the formula I | propamocarb hydrochloride |
| B-177 | a compound of the formula I | 3-(4-chlorophenyl)-3-(2-isopropoxy-carbonylamino-3-methylbutyrylamino)-propionic acid methyl ester |
| B-178 | a compound of the formula I | valiphenal |
| B-179 | a compound of the formula I | 4-fluorophenyl N-(1-(1-(4-cyanophenyl)-ethanesulfonyl)but-2-yl)carbamate |
| B-180 | a compound of the formula I | dodine |
| B-181 | a compound of the formula I | dodine free base |
| B-182 | a compound of the formula I | iminoctadine |
| B-183 | a compound of the formula I | iminoctadine triacetate |
| B-184 | a compound of the formula I | iminoctadine tris(albesilate) |
| B-185 | a compound of the formula I | guazatine |
| B-186 | a compound of the formula I | guazatine acetate |
| B-187 | a compound of the formula I | kasugamycin |
| B-188 | a compound of the formula I | kasugamycin hydrochloride hydrate |
| B-189 | a compound of the formula I | polyoxine |
| B-190 | a compound of the formula I | streptomycin |
| B-191 | a compound of the formula I | validamycin A |
| B-192 | a compound of the formula I | binapacryl |
| B-193 | a compound of the formula I | dicloran |
| B-194 | a compound of the formula I | dinobuton |
| B-195 | a compound of the formula I | dinocap |
| B-196 | a compound of the formula I | nitrothal-isopropyl |
| B-197 | a compound of the formula I | tecnazen |
| B-198 | a compound of the formula I | fentin acetate |
| B-199 | a compound of the formula I | fentin chloride |
| B-200 | a compound of the formula I | fentin hydroxide |

TABLE B-continued

| Line | Component 1 | Component 2 |
|---|---|---|
| B-201 | a compound of the formula I | isoprothiolane |
| B-202 | a compound of the formula I | dithianon |
| B-203 | a compound of the formula I | edifenphos |
| B-204 | a compound of the formula I | fosetyl |
| B-205 | a compound of the formula I | fosetyl aluminum |
| B-206 | a compound of the formula I | iprobenfos |
| B-207 | a compound of the formula I | pyrazophos |
| B-208 | a compound of the formula I | tolclofos-methyl |
| B-209 | a compound of the formula I | chlorothalonil |
| B-210 | a compound of the formula I | dichlofluanid |
| B-211 | a compound of the formula I | dichlorophen |
| B-212 | a compound of the formula I | flusulfamide |
| B-213 | a compound of the formula I | hexachlorobenzene |
| B-214 | a compound of the formula I | pencycuron |
| B-215 | a compound of the formula I | pentachlorophenol and salts thereof |
| B-216 | a compound of the formula I | phthalide |
| B-217 | a compound of the formula I | quintozene |
| B-218 | a compound of the formula I | thiophanate methyl |
| B-219 | a compound of the formula I | tolylfluanid |
| B-220 | a compound of the formula I | N-(4-chloro-2-nitrophenyl)-N-ethyl-4-methylbenzenesulfonamide |
| B-221 | a compound of the formula I | phosphorous acid and its salts |
| B-222 | a compound of the formula I | sulfur |
| B-223 | a compound of the formula I | Bordeaux mixture |
| B-224 | a compound of the formula I | copper acetate |
| B-225 | a compound of the formula I | copper hydroxide |
| B-226 | a compound of the formula I | copper oxychloride |
| B-227 | a compound of the formula I | basic copper sulfate |
| B-228 | a compound of the formula I | biphenyl |
| B-229 | a compound of the formula I | bronopol |
| B-230 | a compound of the formula I | cyflufenamid |
| B-231 | a compound of the formula I | cymoxanil |
| B-232 | a compound of the formula I | diphenylamin |
| B-233 | a compound of the formula I | metrafenon |
| B-234 | a compound of the formula I | mildiomycin |
| B-235 | a compound of the formula I | oxine-copper |
| B-236 | a compound of the formula I | prohexadione-calcium |
| B-237 | a compound of the formula I | spiroxamin |
| B-238 | a compound of the formula I | tolylfluanid |
| B-239 | a compound of the formula I | N-(cyclopropylmethoxyimino-(6-difluoromethoxy-2,3-difluorophenyl)-methyl)-2-phenylacetamide |
| B-240 | a compound of the formula I | N'-(4-(4-chloro-3-trifluoromethylphenoxy)-2,5-dimethylphenyl)-N-ethyl-N-methyl-formamidine |
| B-241 | a compound of the formula I | N'-(4-(4-fluoro-3-trifluoromethylphenoxy)-2,5-dimethylphenyl)-N-ethyl-N-methyl-formamidine |
| B-242 | a compound of the formula I | N'-(2-methyl-5-trifluoromethyl-4-(3-trimethylsilanylpropoxy)phenyl)-N-ethyl-N-methylformamidine |
| B-243 | a compound of the formula I | N'-(5-difluoromethyl-2-methyl-4-(3-trimethylsilanylpropoxy)phenyl)-N-ethyl-N-methylformamidine |

The active compounds II specified above as component 2, their preparation, and their effect against fungal pathogens are widely known (cf.: http://www.hclrss.demon.co.uk/index.html); they are available commercially. The compounds with IUPAC nomenclature, their preparation, and their fungicidal activity are likewise known [cf. EP-A 226 917; EP-A 10 28 125; EP-A 10 35 122; EP-A 12 01 648; WO 98/46608; WO 99/24413; WO 03/14103; WO 03/053145; WO 03/066609; WO 04/049804].

SYNTHESIS EXAMPLES

1) Synthesis of 4-{anti-2-[(1H-1,2,4-triazol-1-yl)methyl]-3-[2-fluorophenyl]oxiran-2-yl}-3-fluorobenzonitrile A solution of anti-2-(4-chloro-2-fluorophenyl)-3-(2-fluorophenyl)oxiran-2-yl)methyl-1H-1,2,4-triazole (300 mg, 0.86 mmol), zinc(II) cyanide (105 mg, 0.86 mmol), tris(dibenzylideneacetone)dipalladium(0) (78 mg, 0.086 mmol) and 2,2'-bis(diphenylphosphino)-1,1'-binaphthyl (111 mg, 0.173 mmol) in NMP (17 ml) was stirred at 200° C. in a microwave oven for 2 hours. After cooling to room temperature, the reaction mixture was added to ice-water (100 ml). The resulting precipitate was filtered off and washed with water (50 ml), and the water was removed azeotropically with acetonitrile. The residue was purified by column chromatography (silica gel, diethyl ether/dichloromethane gradient). The target compound 4-{anti-2-[(1H-1,2,4-triazol-1-yl)methyl]-3-[2-fluorophenyl]oxiran-2-yl}-3-fluorobenzonitrile (62 mg, 21%) was, after pooling of the appropriate fractions and removal of the solvent, obtained in the form of a yellow solid.

H-NMR (300 MHz, CDCl$_3$): δ 7.92 (s, 1H), 7.78 (s, 1H), 7.58-7.52 (m, 1H), 7.48-7.29 (m, 5H), 7.23-7.17 (m, 1H), 4.81 (d, J=15.0 Hz, 1H), 4.33 (s, 1H), 4.09 (d, J=15.0 Hz, 1H).

The compounds of Table 69 were prepared analogously to this procedure.

TABLE 69

| Compound | A | B | Physical data m.p. [° C.] |
|---|---|---|---|
| 69.1 | 3,4-difluorophenyl | 2-cyanophenyl | 194-195 |
| 69.2 | 3-fluorophenyl | 2-cyanophenyl | 183-185 |
| 69.3 | 2-fluoro-4-cyanophenyl | 2-fluorophenyl | 165-167 |

Biological Part
Greenhouse
Preparation of Active Compound

The active compounds were prepared separately or jointly as a stock solution comprising 25 mg of active compound which was made up to 10 ml using a mixture of acetone and/or DMSO and the emulsifier Wettol EM 31 (wetting agent having emulsifying and dispersing action based on ethoxylated alkylphenols) in a volume ratio of solvent/emulsifier of 99:1. The mixture was then made up to 100 ml with water. This stock solution was diluted with the solvent/emulsifier/water mixture described to give the concentration of active compounds stated below.

Use Example 1

Curative Activity Against Soybean Rust Caused by *Phakospora pachyrhizi* (Phakpa K3)

Leaves of potted soybean seedlings were inoculated with a spore suspension of soybean rust (*Phakospora pachyrhizi*). The pots were then placed in a chamber with high atmospheric humidity (90 to 95%) at 23 to 27° C. for 24 hours. During this time, the spores germinated and the germ tubes penetrated into the leaf tissue. Infected plants were placed into a chamber with temperatures between 23 and 27° C. and 60-80% relative atmospheric humidity for a further 2 days. The plants were then sprayed to run off point with the active compound solution described above at the active compound concentration stated below. After the spray coating had dried on, the test plants were cultivated in a greenhouse at temperatures between 23 and 27° C. and 60 to 80% relative atmospheric humidity for 14 days. The extent of the rust fungus development on the leaves was then determined.

The plants which had been treated with an aqueous active compound preparation comprising 63 ppm of the active compounds 69.1 or 69.2 showed an infection of 0%, whereas the untreated plants were 90% infected.

Use Example 2

Protective Activity Against *Puccinia recondita* on Wheat (Brown Rust of Wheat) (Puccrt P1)

Leaves of potted wheat seedlings were sprayed to run off point with an aqueous suspension having the active compound concentration stated below. The next day, the treated plants were inoculated with a spore suspension of brown rust of wheat (*Puccinia recondita*). The plants were then placed in a chamber with high atmospheric humidity (90 to 95%) at 20 to 22° C. for 24 hours. During this time, the spores germinated and the germ tubes penetrated into the leaf tissue. The next day, the test plants were returned to the greenhouse and cultivated at temperatures between 20 and 22° C. and 65 to 70% relative atmospheric humidity for a further 7 days. The extent of the rust fungus development on the leaves was then determined visually.

The plants which had been treated with an aqueous active compound preparation comprising 63 ppm of the active compounds 69.1 or 69.3 showed an infection of 0%, whereas the untreated plants were 90% infected.

Use Example 3

Activity Against Mildew on Cucumber Leaves Caused by *Sphaerotheca fuliginea*, Protected Application (Sphrfu P1)

At the cotyledon stage, leaves of potted cucumber seedlings were sprayed to run off point with an aqueous suspension having the active compound concentration below. 20 hours after the spray coating had dried on, the plants were inoculated with an aqueous spore suspension of mildew of cucumber (*Sphaerotheca fuliginea*). The plants were then cultivated in a greenhouse at temperatures between 20 and 24° C. and 60 to 80% relative atmospheric humidity for 7 days. The extent of the mildew development was then determined visually in % infection of the cotyledon area.

The plants which had been treated with an aqueous active compound preparation comprising 63 ppm of the active compound 69.3 showed an infection of 1%, whereas the untreated plants were 90% infected.

The invention claimed is:

1. A compound of formula I

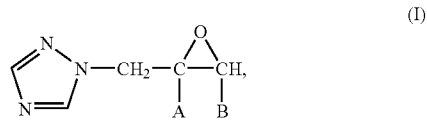

(I)

wherein
A or B is phenyl which is substituted by one CN and optionally by one to three of the following substituents: halogen,
and the respective other substituent
A or B is phenyl which is substituted by one to three of the following substituents:
halogen, $C_1$-$C_4$-alkyl, and $C_1$-$C_4$-alkoxy,
or a plant-compatible acid addition salt or metal salt thereof.

2. The compound of claim 1, wherein said CN-substituted phenyl is additionally substituted by one to three of the following substituents:
halogen, $C_1$-$C_4$-alkyl or $C_1$-$C_4$-alkoxy.

3. The compound of claim 2, wherein said CN-substituted phenyl is additionally substituted by one to three halogen.

4. The compound of claim 3, wherein said CN-substituted phenyl is additionally substituted by one of the following substituents: halogen, $NO_2$, amino, $C_1$-$C_4$-alkyl, $C_1$-$C_4$-alkoxy, $C_1$-$C_4$-haloalkyl, $C_1$-$C_4$-haloalkoxy, $C_1$-$C_4$-alkylamino, $C_1$-$C_4$-dialkylamino, thio or $C_1$-$C_4$-alkylthio.

5. The compound of claim 1, wherein said respective other phenyl is substituted by one to three of the following substituents: halogen.

6. The compound of claim 1, wherein said respective other phenyl is substituted by one to three of the following substituents: $C_1$-$C_4$-alkyl.

7. The compound of claim 1, wherein said respective other phenyl is substituted by one to three of the following substituents: $C_1$-$C_4$-alkoxy.

8. A crop protection composition comprising an acceptable solvent, auxiliary or carrier and a compound of formula I of claim 1 and/or an acid addition salt or metal salt thereof.

9. A seed comprising a coating of at least one compound of formula of claim 1 and/or an acid addition salt or metal salt thereof and an agriculturally acceptable carrier.

10. A method for controlling phytopathogenic fungi comprising applying an agronomically effective and non-phytotoxic quantity of a compound of claim 1 to soil where a plant grows and/or is capable of growing, to leaves, and/or to fruits of a plant and/or to a seed of a plant.

* * * * *